US00PP23557P2

(12) United States Plant Patent
Olesen

(10) Patent No.: US PP23,557 P2
(45) Date of Patent: Apr. 23, 2013

(54) COMPACT FLORIBUNDA ROSE PLANT NAMED 'POULCAS033'

(50) Latin Name: ***Rosa* hybrid**
Varietal Denomination: Poulcas033

(75) Inventor: Mogens Nyegaard Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 13/317,240

(22) Filed: Oct. 13, 2011

(51) Int. Cl.
*A01H 5/00* (2006.01)

(52) U.S. Cl. ..... Plt./145

(58) Field of Classification Search ..... Plt./145
See application file for complete search history.

*Primary Examiner* — Annette Para

(57) ABSTRACT

A new garden rose plant of the compact floribunda class which has abundant, yellow flowers and attractive foliage. This new and distinct variety has shown to be uniform and stable in the resulting generations from asexual propagation.

4 Drawing Sheets

Botanical designation: *Rosa* hybrid.
Variety denomination: 'Poulcas033'.

SUMMARY OF THE INVENTION

The present invention constitutes a new and distinct variety of garden rose plant which originated from a controlled crossing between the female seed parent, an unnamed seedling, and the male pollen parent, an unnamed seedling.

The two parents were crossed during the summer of 2001 and the resulting seeds were planted in a controlled environment in Fredensborg, Denmark. The new variety, named 'Poulcas033', originated as a single seedling from the stated cross.

The new variety may be distinguished from its female seed parent primarily by flower color. The seed parent has pink flowers while the new variety has light yellow flowers.

The new variety may be distinguished from its male pollen parent primarily by flower color. The pollen parent has pink flowers while the new variety has light yellow flowers.

The objective of the hybridization of this rose variety was to create a new and distinct variety for garden use with unique qualities, such as:

1. Uniform and abundant yellow flowers;
2. Vigorous, but compact growth when propagated both as a budded rose and on its own roots;
3. Exceptional disease resistance.
4. Strong perfume.

This combination of qualities is not present in previously available commercial cultivars of this type, known to the inventor, and distinguish 'Poulcas033' from all other varieties of which we are aware.

As part of the rose development program, Mogens N. Olesen germinated the seeds from the aforementioned hybridization during winter of 2001 and conducted evaluations on the resulting seedlings in a controlled environment in Fredensborg, Denmark. 'Poulcas033' was selected in the spring of 2002 by the inventor as a single plant from the progeny of the aforementioned hybridization.

Asexual reproduction of 'Poulcas033' by traditional budding and rooted cuttings was first done by Mogens N. Olesen in the nursery in Fredensborg, Denmark in July, 2002. This initial and other subsequent asexual propagations conducted in controlled environments have demonstrated that the characteristics of 'Poulcas033' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems, of 'Poulcas033'. Specifically illustrated in the drawing are.

DETAILED DESCRIPTION OF THE VARIETY

Figure 1:
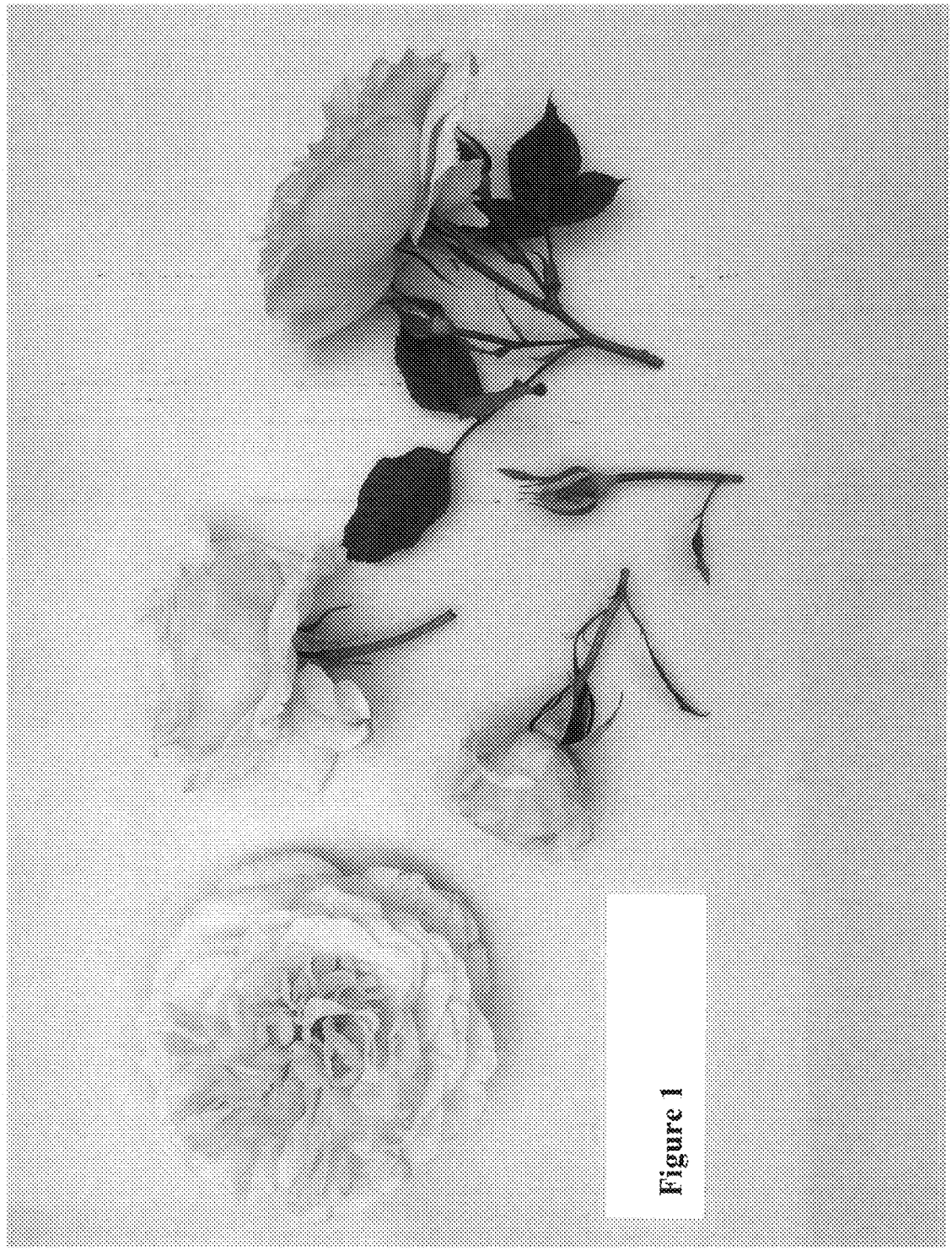
FIG. 1; Open flowers and flower buds.
Figure 2:
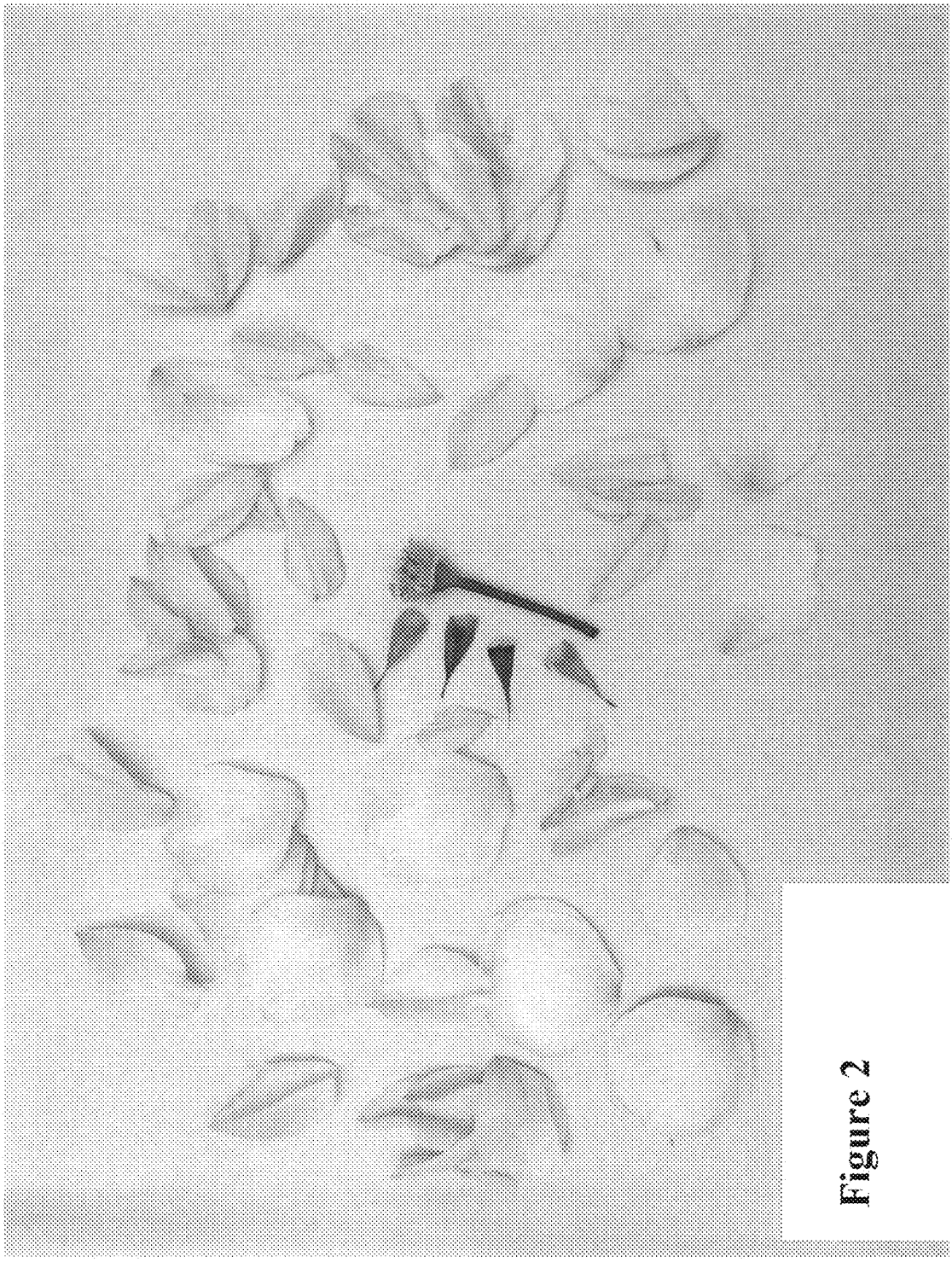
FIG. 2; Petals detached, sepals, and peduncle with flower parts.
Figure 3:
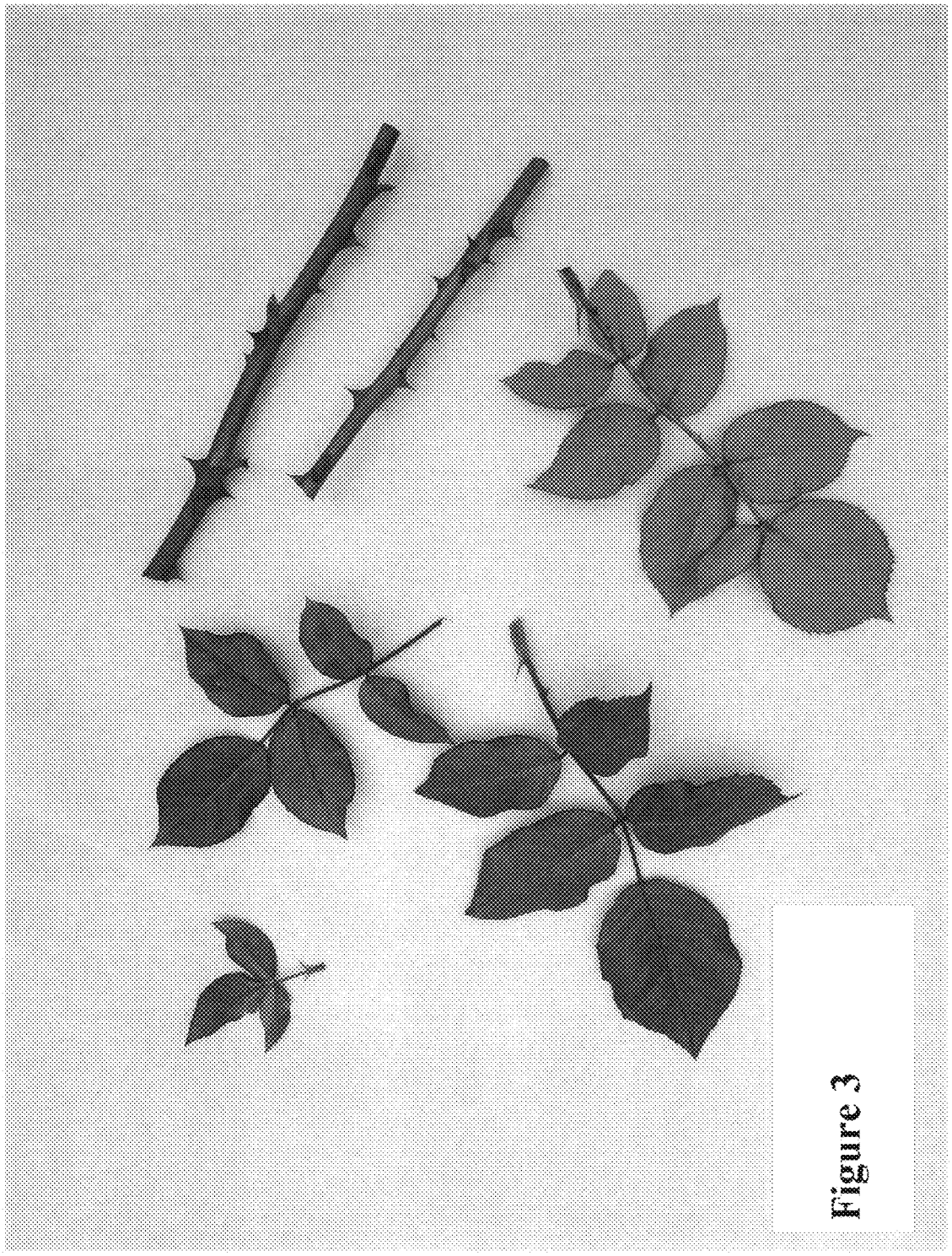
FIG. 3; Leaves and stems.
Figure 4:
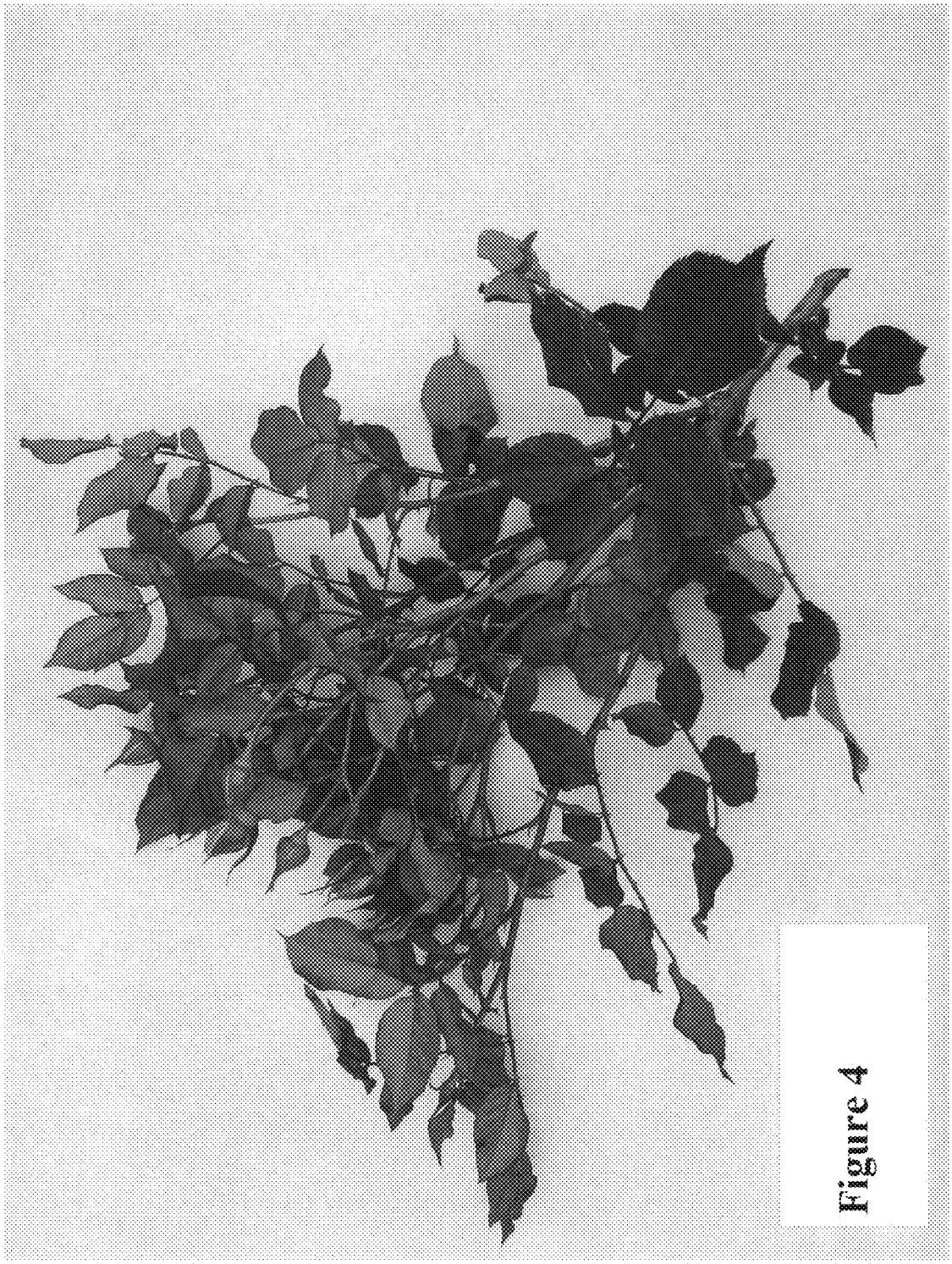
FIG. 4; Flowering branch.

The following is a description of 'Poulcas033', as observed in its growth in in a field nursery in Benton county, Oreg. Observed plants are 3 years of age, and were grown on *Rosa multiflora* understock. Color references are made using The Royal Horticultural Society (London, England) Colour Chart, 2001, except where common terms of color are used.

For a comparison, several physical characteristics of the rose variety 'Poulcas025', U.S. Plant Pat. No. 18,499 are compared to 'Poulcas033' in Chart 1.

CHART 1

| | 'Poulcas033' | 'Poulcas025' |
|---|---|---|
| Flower color, general tonality | Yellow Group 11D with intonations of Yellow-Orange Group 16B. | Yellow Group 4B at center with Yellow Group 4D at the periphery. |
| Flower Diameter | 110 to 130 mm when open. | 20 mm. |
| Scent | Strong perfumed scent, similar to licorice or anise. | Medium floral scent. |

FLOWER AND FLOWER BUD

Blooming habit: Continuous.

Flower bud:

*Size*.—Upon opening, 30 mm in length from base of receptacle to end of bud. Bud diameter is 18 mm.

*Bud form*.—Ovoid.

*Bud color*.—As sepals unfold, petals are Green-Yellow Group 1C with intonations of Orange-Red Group N34A.

*Sepal inner surface*.—Color: Yellow-Green Group 145B. At margins, sepals are Yellow-Green Group 147B. Weak anthocyanin the color of Greyed-Purple Group 184C. Surface: Medium pubescence observed.

*Sepal outer surface*.—Color: Yellow-Green Group 144A. Anthocyanic pigments the color of Greyed-Red Group 181A observed. Texture: Smooth.

*Sepal shape*.—Apex: Cirrhose. Base: Flat at union with receptacle.

*Sepal margin*.—Margins have strong weak foliaceous appendages on three of the five sepals.

*Sepal size*.—30 mm long by 11 mm wide.

*Receptacle*.—Texture: Smooth. Shape: Campanulate. Size: 10 mm tall by 10 mm wide. Color: Yellow-Green Group 144A. Anthocyanic pigments the color of Greyed-Purple Group 183C observed.

*Peduncle*.—Length: 80 to 130 mm. Diameter: 3 to 4 mm. Color: Yellow-Green Group 144B with moderate anthocyanic pigments Greyed-Purple Group 183B. Surface: Smooth.

*Pedicel*.—Surface: Somewhat rough with many stipitate glands. Length: 40 to 44 mm on average. Diameter: 3 to 4 mm on average. Color: Yellow-Green Group 144B with strong to moderate anthocyanic pigments the color of Greyed-Purple Group 184A observed. Strength: Strong.

Flower bud development: Flower buds are borne in a corymb of 3 to 5 flower buds per flowering stem.

Flower bloom:

*Fragrance*.—Strong perfumed scent, similar to licorice or anise.

*Duration*.—The blooms have a duration on the plant of approximately 10 days. Petals fall cleanly away from plant after flowers have fully matured.

*Size*.—Flower diameter is 110 to 130 mm when open. Flower depth is 50 mm.

*Flower shape*.—When flowers are opening, the shape is generally a classic hybrid tea. Afterwards, the blooms open fully becoming rosettes with many petals packed into sections.

*Shape of flower, side view*.—Upon opening the upper portion is flat. The lower portion is flat.

Petalage: Under normal conditions, flowers have 100 petals total, 30 on average of which are petaloids.

Petal color:

*Upon opening, outer petals*.—Upper surface: Yellow Group 11D. Yellow Group 9A splashed at the basal zone becoming Yellow Group 10A at the middle zone. There are light intonations of Red Group 38C at the petal margin. Lower surface: Yellow Group 11D. Yellow Group 13C splashed at the basal zone and middle zone. Weak intonations of Red Group 38C at margins.

*Upon opening, inner petals*.—Upper surface: Yellow Group 12D. Yellow 12A at basal zone. Lower surface: Yellow 12B at basal and middle zone. Yellow-Orange Group 19C at marginal zone.

*After opening, outer petals*.—Upper surface: White Group 155B blended with Green-White Group 157D at middle zone. Lower surface: White Group 155B blended with Green-White Group 157D at middle zone. No other distinctive coloration at the petal base observed.

*After opening, inner petals*.—Upper surface: Yellow Group 9A at basal zone. Yellow Group 12C at middle zone. Yellow Group 11B at margin. Lower surface: Yellow Group 13C at basal zone. Yellow Group 12C at middle zone. Yellow Group 11D at margin.

*Basal petal spots, after opening*.—Upper surface: Yellow Group 9B. Lower surface: Yellow Group 12B.

General tonality: On open flower Yellow Group 11D with intonations of Yellow-Orange Group 16B. General tonality changes to Yellow Group 11D with intonations of Yellow Group 12B after a period of 5 to 7 days.

Petals:

*Petal reflex*.—Weakly reflexed.

*Margin*.—Entire and uniform. Weak undulations of margin observed.

*Shape*.—Generally broad elliptic. Apex shape: Rounded. Base shape: Rounded.

*Size*.—Outer petals are 55 mm long by 60 mm wide. Inner petals are 30 mm long by 25 mm wide.

*Texture*.—Smooth.

*Thickness*.—Average.

Petaloids:

*Quantity*.—30 on average.

*Shape*.—Elliptic. Acute at the apex and base.

*Color*.—Upper Yellow Group 12A. Lower Yellow Group 13B.

*Size*.—30 mm (l)×20 mm (w).

Reproductive organs:

*Pollen*.—None observed.

*Anthers*.—Size: 2 mm in length. Color: Yellow-Orange Group 14B. Quantity: 70 on average.

*Filaments*.—Color: Yellow-Orange Group 14B. Length: 6 mm.

*Pistils*.—Length: 7 mm. Quantity: About 80.

*Stigmas*.—Superior in location relative to the length of the filaments and the height of the anthers. Color: Greyed-Yellow Group 160C.

*Styles*.—Color: Red Group 47A.

*Hips*.—None observed.

PLANT

Plant growth: Upright and bushy. When grown as a budded field grown plant on *Rosa multiflora* understock, the average height of the plant is 70 cm and the average width is 70 cm.

Stems:

*Color*.—Juvenile growth: Yellow-Green Group 144C with anthocyanic intonations of Greyed-Orange Group 174A. Mature growth: Yellow-Green Group 144B.

*Length*.—On average, canes are 45 cm from the base of the plant to the flowering portion.

*Diameter*.—6 to 8 mm.

*Internodes*.—On mature canes, there is an average distance of 50 mm between nodes.

*Surface texture*.—Young wood: Smooth. Older wood: Smooth.

Prickles:

*Incidence*.—5 to 11 prickles per 10 cm of stem.

*Size*.—Average length of prickles on mature stems is 8 mm.

*Shape*.—Concave.

*Color*.—Juvenile prickles: Greyed-Red Group 182A. Mature prickles: Greyed-Red Group 181A.

Plant foliage: Normal number of leaflets leaves in middle of the stem: 5 leaflets.

*Compound leaf*.—180 mm (l)×130 (w).

*Quantity*.—3 leaves per 10 cm of stem on average.

*Color of mature foliage*.—Upper side: Yellow-Green Group 146A. Lower side: Yellow-Green Group 146B.

*Color of juvenile foliage*.—Upper side: Yellow-Green Group 144A. Lower side: Yellow-Green Group 144B. Anthocyanin: Greyed-Purple Group 183B at the margins and generalized throughout the juvenile leaflets.

Plant leaves and leaflets:

*Stipules*.—Size: 35 mm in length. Quantity: 2 per compound leaf. Shape: Linear, slightly broad based with outward extending apices. Margins: Many stipitate glands. Color: Yellow-Green Group 144B.

*Petiole*.—Length: 55 mm on average. Diameter: 2 mm.

*Upper surface*.—Color: Greyed-Orange Group 174A. Observations: Numerous stipitate glands and prickles observed.

*Lower surface*.—Color: Yellow-Green Group 144B.

*Rachis*.—Length: 55 mm on average. Upper surface: Greyed-Orange Group 174A. Observations: Numerous stipitate glands and prickles observed.

*Lower surface*.—Color: Yellow-Green Group 144B.

*Leaflet*.—Edge: Doubly Serrated. Size: The terminal leaflet on normal leaves is 70 to 15 mm in length by 45 to 50 mm wide. Shape: Generally elliptic to orbicular. Base: Rounded. Apex: Caudate. Texture: Smooth. Thickness: Above average. Arrangement: Odd pinnate. Venation: Reticulate. Glossiness: Moderately glossy.

Disease resistance: Above average resistance to powdery and downy mildew, rust, black spot, and *Botrytis* under normal growing conditions in Benton county, Oreg.

Cold hardiness: The variety is tolerant to USDA Cold Hardiness Zone 6.

Heat tolerance: The variety has been found to be suitable for climate conditions found in the American Horticulture Society heat zone 7.

The invention claimed is:

1. A new and distinct variety of rose plant of the compact floribunda rose class named 'Poulcas033', substantially as illustrated and described herein, due to its abundant yellow flowers, disease resistance, and extended period of bloom.

* * * * *